(12) United States Patent
Jeong et al.

(10) Patent No.: US 12,357,559 B2
(45) Date of Patent: Jul. 15, 2025

(54) COSMETIC COMPOSITION FOR PREVENTING SKIN AGING AND REDUCING SKIN WRINKLES, COMPRISING VIBURNUM STELLATO-TOMENTOSUM EXTRACT

(71) Applicant: KOREA RESEARCH INSTITUTE OF BIOSCIENCE AND BIOTECHNOLOGY, Daejeon (KR)

(72) Inventors: Tae Sook Jeong, Daejeon (KR); Ho Yong Park, Daejeon (KR); Hwa Lee, Daejeon (KR); Soo Yong Kim, Daejeon (KR); Rosales Ovares Kattia, Santo Domingo (CR); Zamora Villalobos Nelson, Santo Domingo (CR); Sang Ho Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 617 days.

(21) Appl. No.: 17/774,522

(22) PCT Filed: Nov. 6, 2020

(86) PCT No.: PCT/KR2020/015463
§ 371 (c)(1),
(2) Date: Oct. 25, 2022

(87) PCT Pub. No.: WO2021/091284
PCT Pub. Date: May 14, 2021

(65) Prior Publication Data
US 2023/0073286 A1 Mar. 9, 2023

(30) Foreign Application Priority Data
Nov. 6, 2019 (KR) .................. 10-2019-0141268

(51) Int. Cl.
*A61K 36/00* (2006.01)
*A61K 8/9789* (2017.01)
*A61Q 19/08* (2006.01)

(52) U.S. Cl.
CPC ............ *A61K 8/9789* (2017.08); *A61Q 19/08* (2013.01)

(58) Field of Classification Search
CPC ..................................................... A61Q 19/08
See application file for complete search history.

(56) References Cited

U.S. PATENT DOCUMENTS

2015/0224049 A1  8/2015  Florence et al.

FOREIGN PATENT DOCUMENTS

| KR | 10-2009-0097232 A | 9/2009 |
|---|---|---|
| KR | 10-2013-0034720 A | 4/2013 |
| KR | 101398392 B1 | 5/2014 |
| KR | 10-1994557 B1 | 6/2019 |
| WO | 2009120214 A1 | 10/2009 |

OTHER PUBLICATIONS

International Search Report corresponding to PCT/KR2020/015463; dated Apr. 9, 2021 (5 pages, including English translation).

*Primary Examiner* — Qiuwen Mi
(74) *Attorney, Agent, or Firm* — Myers Bigel, P.A.

(57) ABSTRACT

The present invention relates to a cosmetic composition for preventing skin aging and reducing skin wrinkles containing an extract of *Viburnum stellato-tomentosum*. The cosmetic composition has an excellent antioxidant effect and exhibits the effect of inhibiting collagenase overexpression and increasing collagen gene expression, and thus can be effectively used for the purposes of preventing skin aging and reducing skin wrinkles.

8 Claims, 9 Drawing Sheets

Specification includes a Sequence Listing.

VS: *V. stellato-tomentosum*
VL: *V. lantana* L.
VO: *V. opulus var.* Sargentii (Koehne) Takeda
VD: *V. dilatatum* Thunb.

```
                         SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Actin_forward

<400> SEQUENCE: 1
ggcaccacac cttctacaat                                                   20

<210> SEQ ID NO 2
<211> LENGTH: 20
<212> TYPE: DNA
<213> ORGANISM: Artificial Sequence
<220> FEATURE:
<223> OTHER INFORMATION: Actin_reverse

<400> SEQUENCE: 2
gcctggatag caacgtacat                                                   20

<210> SEQ ID NO 3
<211> LENGTH: 26
<212> TYPE: DNA
<213> ORGANISM: Artificial Sequence
<220> FEATURE:
<223> OTHER INFORMATION: MMP-1_forward

<400> SEQUENCE: 3
aacacatctg acctacagga ttgaaa                                            26

<210> SEQ ID NO 4
<211> LENGTH: 23
<212> TYPE: DNA
<213> ORGANISM: Artificial Sequence
<220> FEATURE:
<223> OTHER INFORMATION: MMP-1_reverse

<400> SEQUENCE: 4
cttggtgaat gtcagaggtg tga                                               23

<210> SEQ ID NO 5
<211> LENGTH: 26
<212> TYPE: DNA
<213> ORGANISM: Artificial Sequence
<220> FEATURE:
<223> OTHER INFORMATION: MMP-2_forward

<400> SEQUENCE: 5
actggagcaa aaacaagaag acatac                                            26

<210> SEQ ID NO 6
<211> LENGTH: 24
<212> TYPE: DNA
<213> ORGANISM: Artificial Sequence
<220> FEATURE:
<223> OTHER INFORMATION: MMP-2_reverse

<400> SEQUENCE: 6
tccattttct tcttcacctc attg                                              24
```

```
<210> SEQ ID NO 7
<211> LENGTH: 19
<212> TYPE: DNA
<213> ORGANISM: Artificial Sequence
<220> FEATURE:
<223> OTHER INFORMATION: COL1A1_forward

<400> SEQUENCE: 7
tggcctcgga ggaaactttt                                             19

<210> SEQ ID NO 8
<211> LENGTH: 21
<212> TYPE: DNA
<213> ORGANISM: Artificial Sequence
<220> FEATURE:
<223> OTHER INFORMATION: COL1A1_reverse

<400> SEQUENCE: 8
gcttccccat catctccatt c                                           21

<210> SEQ ID NO 9
<211> LENGTH: 22
<212> TYPE: DNA
<213> ORGANISM: Artificial Sequence
<220> FEATURE:
<223> OTHER INFORMATION: COL1A2_forward

<400> SEQUENCE: 9
cggtggtggt tatgactttg gt                                          22

<210> SEQ ID NO 10
<211> LENGTH: 23
<212> TYPE: DNA
<213> ORGANISM: Artificial Sequence
<220> FEATURE:
<223> OTHER INFORMATION: COL1A2_reverse

<400> SEQUENCE: 10
gaagggtctc aatctggttg ttg                                         23
```

COSMETIC COMPOSITION FOR PREVENTING SKIN AGING AND REDUCING SKIN WRINKLES, COMPRISING VIBURNUM STELLATO-TOMENTOSUM EXTRACT

CROSS REFERENCE TO RELATED APPLICATIONS

This application is a 35 U.S.C. § 371 national stage application of PCT International Application No. PCT/KR2020/015463, filed Nov. 6, 2020, which claims priority from Korean Patent Application No. 10-2019-0141268, filed Nov. 6, 2019, the contents of which are incorporated herein in their entireties by reference.

STATEMENT REGARDING ELECTRONIC FILING OF A SEQUENCE LISTING

A Sequence Listing in ASCII text format, submitted under 37 C.F.R. § 1.821, entitled 1433-58 ST25.txt, 2,407 bytes in size, generated on Oct. 24, 2022, and filed via EFS-Web, is provided in lieu of a paper copy. This Sequence Listing is hereby incorporated herein by reference into the specification for its disclosures.

TECHNICAL FIELD

The present invention relates to a cosmetic composition for preventing skin aging and reducing skin wrinkles containing an extract of *Viburnum stellato-tomentosum*.

BACKGROUND ART

The causes of human skin aging are classified into two types: intrinsic aging and photo-aging. Among them, photo-aging refers to skin aging caused mainly by ultraviolet rays.

In general, ultraviolet rays are classified according to their wavelengths into three types: ultraviolet A (UVA, 320 to 400 nm), ultraviolet B (UVB, 280 to 320 nm), and ultraviolet C (UVC, 190 to 280 nm). Among ultraviolet rays reaching the surface from sunlight, ultraviolet C is absorbed, scattered and filtered by the ozone layer in the upper atmosphere, and thus does not have a significant effect on natural photochemical reactions. Ultraviolet A primarily comes from the sun, but is also emitted from artificial lamps, etc., and penetrates deep into the epidermal and dermal layers of the skin. Meanwhile, it is known that UVB has a shorter wavelength than UVA and does not penetrate deep into the skin. However, it is known that UVB has much stronger energy than UVA, and thus is a wavelength that promotes photo-aging of the skin while inducing sharp erythema on the skin surface.

Collagen is a major matrix protein produced in fibroblasts of the skin. It is an important protein that is present in the extracellular matrix and accounts for 30% of the total weight of the proteins in the body. It also has a rigid triple-helical structure. It is known that collagen mainly functions to give mechanical firmness to the skin, strengthen connective tissue, bind tissues, maintain cell adhesion, and induce cell division and differentiation. It is known that collagen is also destroyed by UV exposure, which is an external cause of skin aging, and that changes in collagen due to UV rays are proportional to the time of exposure to UV rays. Ultraviolet rays accumulate elastic fibrous materials in the dermal layer of the skin and denature collagen fibers, causing wrinkles in the skin and reducing skin elasticity.

Matrix metalloproteinases (MMPs) play a key role in the process of skin aging caused by UV rays. Expression of MMPs is induced by UV irradiation, and MMPs cause the degradation of collagen fibers including collagen in the skin tissue, resulting in skin aging including wrinkle formation. Among them, MMP-1 is an enzyme that degrades type I collagen, which accounts for more than 90% of collagen distributed in the human body, as well as type II and III collagen. It is well known as a target for ameliorating skin aging and reducing wrinkle formation. MMP-2 is also an enzyme that degrades type IV collagen that forms a basement membrane, and it has been studied as a target for ameliorating skin aging (*Int J Mol Sci*. 2016; 17, 868). MMP-2 µlays a major role in skin aging by degrading collagen fragments, caused by MMP-1, into smaller fragments (*J Appl Biol Chem*. 2018; 61, 9-15).

In addition, in skin aging, not only MMPs, but also free radicals generated during the body's metabolic process, generation of hydrogen peroxide or peroxides, and oxidation of cell and tissue constituents by destruction of the antioxidant defense mechanism in vivo are involved. Damage to skin cells and tissue occurs due to such factors, and aging of the skin is accelerated.

*Viburnum stellato-tomentosum* is a plant native to Costa Rica and Panama and is known to be used as a food. Although the botanical classification of *Viburnum stellato-tomentosum* is known, but the efficacy thereof is not known.

Accordingly, the present inventors have conducted studies to discover materials for preventing skin aging and reducing skin wrinkles, thereby completing the present invention.

DISCLOSURE

Technical Problem

An object of the present invention is to provide a cosmetic composition for preventing skin aging and reducing skin wrinkles containing an extract of *Viburnum stellato-tomentosum*.

Another object of the present invention is to provide the use of an extract of *Viburnum stellato-tomentosum* in preparation of a cosmetic composition for preventing skin aging and reducing skin wrinkles.

Technical Solution

One aspect of the present invention provides a cosmetic composition for preventing skin aging and reducing skin wrinkles containing an extract of *Viburnum stellato-tomentosum*.

According to one embodiment of the present invention, the extract may be obtained by extraction with any one solvent selected from the group consisting of water, an alcohol having 1 to 4 carbon atoms, and a mixed solvent thereof.

According to one embodiment of the present invention, the extract may be an ethanol extract or a methanol extract.

According to one embodiment of the present invention, the extract may be an ethyl acetate fraction of an ethanol extract of *Viburnum stellato-tomentosum*.

According to one embodiment of the present invention, the skin aging and the skin wrinkles may be caused by skin exposure to UV rays.

According to one embodiment of the present invention, the skin aging and the skin wrinkles may be caused by overexpression of MMP-1 or MMP-2.

According to one embodiment of the present invention, the skin aging and the skin wrinkles may be caused by inhibition of COL1A1 or COL1A2 expression.

According to one embodiment of the present invention, the cosmetic composition may be any one formulation selected from the group consisting of a solution, suspension, emulsion, paste, gel, cream, lotion, powder, soap, surfactant-containing cleansing, oil, powder foundation, emulsion foundation, wax foundation, and spray.

Another aspect of the present invention provides the use of an extract of *Viburnum stellato-tomentosum* in preparation of a cosmetic composition for preventing skin aging and reducing skin wrinkles.

Advantageous Effects

The cosmetic composition for preventing skin aging and reducing skin wrinkles containing an extract of *Viburnum stellato-tomentosum* has an excellent antioxidant effect and exhibits the effects of inhibiting overexpression of collagenase and increasing the expression of collagen genes. Thus, it may be effectively used to prevent skin aging and reduce skin wrinkles.

BEST MODE

Figure 1:
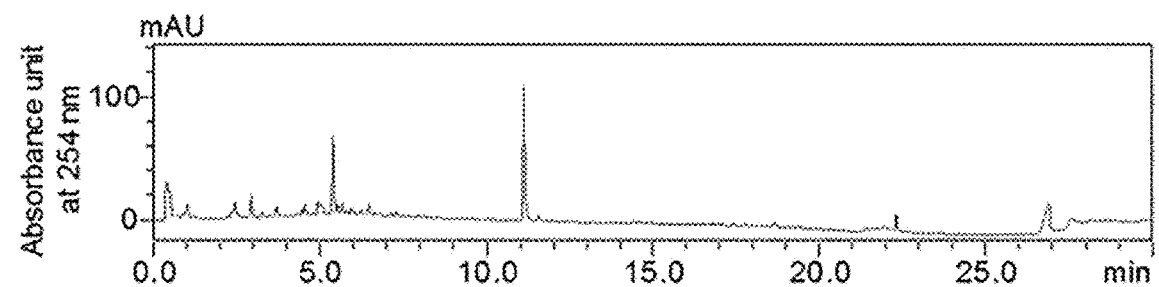
FIG. 1 is a graph showing the HPLC profile of 70% ethanol extract of *Viburnum stellato-tomentosum*.

One aspect of the present invention provides a cosmetic composition for preventing skin aging and reducing skin wrinkles containing an extract of *Viburnum stellato-tomentosum*.

According to one embodiment of the present invention, the extract may be obtained by extraction with any one solvent selected from the group consisting of water, an alcohol having 1 to 4 carbon atoms, and a mixed solvent thereof.

According to one embodiment of the present invention, the extract may be an ethanol extract or a methanol extract.

According to one embodiment of the present invention, the extract may be an ethyl acetate fraction of an ethanol extract of *Viburnum stellato-tomentosum*.

The extract contained in the composition according to the present invention may be obtained as follows. *Viburnum stellato-tomentosum* is washed with water to remove foreign substances, and then dried in the shade, and an appropriate amount of a solvent is added to the *Viburnum stellato-tomentosum* so that the *Viburnum stellato-tomentosum* is completely immersed. At this time, the *Viburnum stellato-tomentosum* may be used as it is in a dried state or may be used in powder form after pulverization. *Viburnum stellato-tomentosum* may be extracted with a conventional extraction solvent. Preferably, it may be extracted with the following solvent: (a) an anhydrous or hydrous lower alcohol having 1 to 4 carbon atoms (e.g., methanol, ethanol, propanol, butanol, normal-propanol, iso-propanol, normal-butanol, etc.); (b) a mixed solvent of the lower alcohol and water; (c) acetone; (d) ethyl acetate; (e) chloroform; (f) 1,3-butylene glycol; (g) hexane; (h) diethyl ether; (i) butyl acetate; (j) chloroform-methanol; or (k) distilled water. Preferably, it may be extracted with either an aqueous ethanol solution (70% or 95%(v/v) ethanol) obtained by mixing ethanol and water at a volume ratio of 70: 30 to 95: 5, or ethyl acetate. During extraction, *Viburnum stellato-tomentosum* may be impregnated at room temperature or warmed.

According to one embodiment of the present invention, the skin aging and the skin wrinkles may be caused by skin exposure to UV rays.

According to one embodiment of the present invention, the skin aging and the skin wrinkles may be caused by overexpression of MMP-1 or MMP-2, and the skin aging and the skin wrinkles may be caused by inhibition of COL1A1 or COL1A2 expression.

The *Viburnum stellato-tomentosum* extract of the present invention exhibits remarkable DPPH radical scavenging activity, exhibits an activity of inhibiting the UV-induced overexpression of MMP-1 and MMP-2 in human skin cells, and exhibits an activity of restoring the UV-induced inhibition of expression of COL1A1 and COL1A2 in human skin cells. Thus, it may effectively ameliorate skin aging by inhibiting the degradation of protein such as skin collagen, which is damaged by UV rays or the like.

According to one embodiment of the present invention, the cosmetic composition may be any one formulation selected from the group consisting of a solution, suspension, emulsion, paste, gel, cream, lotion, powder, soap, surfactant-containing cleansing, oil, powder foundation, emulsion foundation, wax foundation, and spray.

For example, the cosmetic composition of the present invention may be formulated into a solution, suspension, emulsion, paste, gel, cream, lotion, powder, soap, surfactant-containing cleansing, oil, powder foundation, emulsion foundation, wax foundation, and spray, without being limited thereto. More specifically, it may be formulated into skin care cosmetics such as softening lotion, nourishing lotion, lotion, body lotion, nourishing cream, massage cream, moisture cream, hand cream, essence, eye cream, cleansing cream, cleansing foam, cleansing water, pack, gel, patch, oil-in-water (O/W) type emulsion, or water-in-oil (W/O) type emulsion, color cosmetics such as lipstick, makeup base or foundation, hair fixatives such as hair tonic, gel or mousse, or hair cosmetic compositions such as hair restorers or hair dyes.

When the formulation of the present invention is a paste, cream or gel, animal oil, vegetable oil, wax, paraffin, starch, tragacanth, a cellulose derivative, polyethylene glycol, silicone, bentonite, silica, talc or zinc oxide may be used as a carrier component.

When the formulation of the present invention is a powder or spray, it may contain, as a carrier component, lactose, talc, silica, aluminum hydroxide, calcium silicate or polyamide powder. In particular, when the formulation is a spray, it may additionally contain a propellant such as chlorofluorohydrocarbon, propane/butane, or dimethyl ether.

When the formulation of the present invention is a solution or emulsion, it may contain, as a carrier component, a solvent, solubilizer or emulsifier. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol, or fatty acid ester of sorbitan may be used.

When the formulation of the present invention is a suspension, it may contain, as a carrier component, a liquid diluent such as water, ethanol or propylene glycol, a suspending agent such as ethoxylated isostearyl alcohol, polyoxyethylene sorbitol ester, or polyoxyethylene sorbitan ester, microcrystalline cellulose, aluminum metahydroxide, bentonite, agar, or tragacanth.

When the formulation of the present invention is a surfactant-containing cleansing, it may contain, as a carrier component, aliphatic alcohol sulfate, aliphatic alcohol ether sulfate, sulfosuccinic acid monoester, isethionate, an imidazolinium derivative, methyl taurate, sarcosinate, fatty acid amide ether sulfate, alkylamidobetaine, aliphatic alcohol, fatty acid glyceride, fatty acid diethanolamide, vegetable oil, a lanolin derivative, or ethoxylated glycerol fatty acid ester.

When the cosmetic composition of the present invention is a soap, surfactant-containing cleansing or surfactant-free cleansing formulation, it may be applied to the skin and then wiped off, removed, or washed off with water. Examples of the soap include, but are not limited to, liquid soap, powdered soap, solid soap, and oil soap, and examples of the surfactant-containing cleansing formulation include, but are not limited to, cleansing foam, cleansing water, cleansing towel, and cleansing pack. Examples of the surfactant-free cleansing formulation include, but are not limited to, cleansing cream, cleansing lotion, cleansing water, and cleansing gel.

Another aspect of the present invention provides the use of an extract of *Viburnum stellato-tomentosum* in preparation of a cosmetic composition for preventing skin aging and reducing skin wrinkles.

Mode for Invention

Hereinafter, the present invention will be described in more detail with reference to one or more examples. However, these examples are for illustrating the present invention, and the scope of the present invention is not limited to these examples.

EXAMPLE 1

Preparation of Extracts of *Viburnum stellato-tomentosum*

Each of the aerial, stem, flower, leaf, and fruit parts of *Viburnum stellato-tomentosum* (Oerst.) Hemsl. (native to Costa Rica) was collected and dried at room temperature. Each of the dried products was cut to an appropriate size and pulverized using a blender/mixer.

The pulverized product of each of the aerial, stem, flower, leaf, and fruit parts of *Viburnum stellato-tomentosum* was added to a 70% or 95% (v/v) ethanol aqueous solution in an amount of 10 g (pulverized product) per 100 ml (ethanol aqueous solution) and extracted with stirring at room temperature for 48 hours, and then only the portion dissolved in the solvent was collected through filter paper (Whatman, No. 2). The whole extracts were concentrated under reduced pressure to obtain ethanol aqueous extracts of *Viburnum stellato-tomentosum*.

Figure 2:
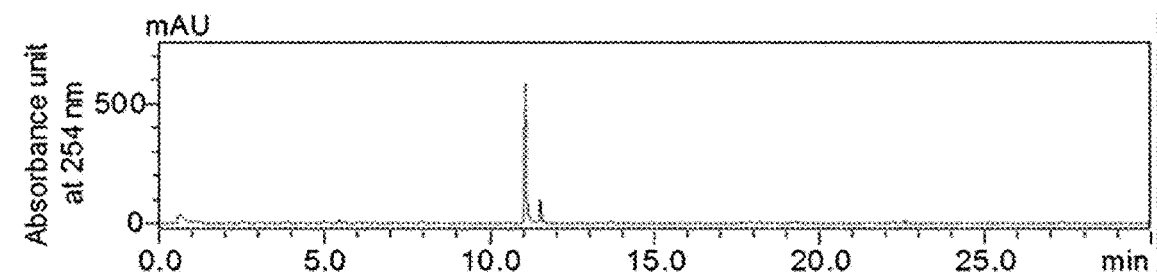
FIG. 2 is a graph showing the HPLC profile of 95% ethanol extract of *Viburnum stellato-tomentosum*.
Figure 3:
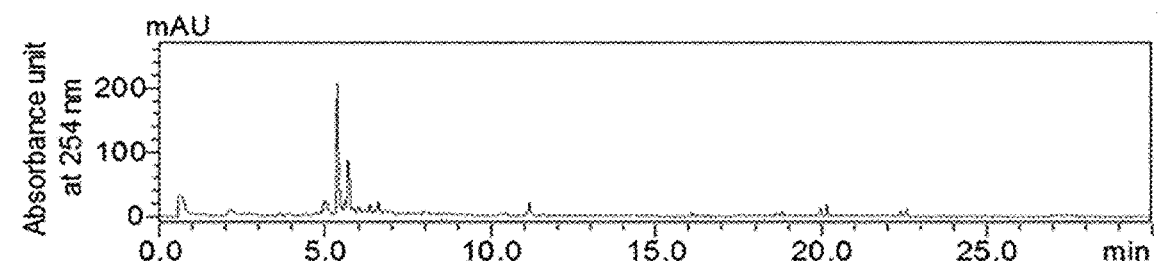
FIG. 3 is a graph showing the HPLC profile of 95% ethanol extract of *Viburnum lantana*.
Figure 4:
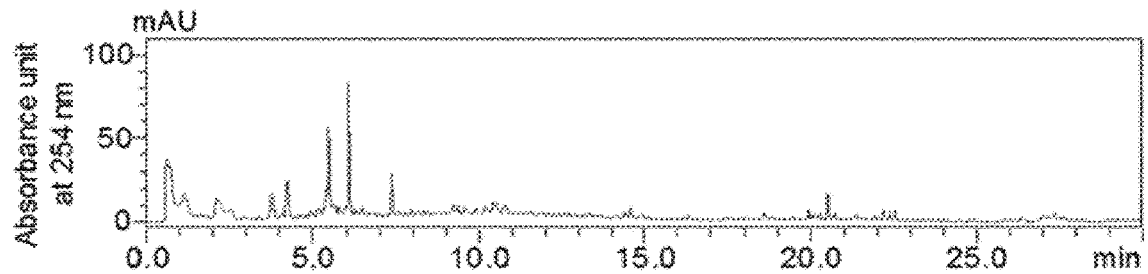
FIG. 4 is a graph showing the HPLC profile of 95% ethanol extract of *Viburnum opulus*.
Figure 5:
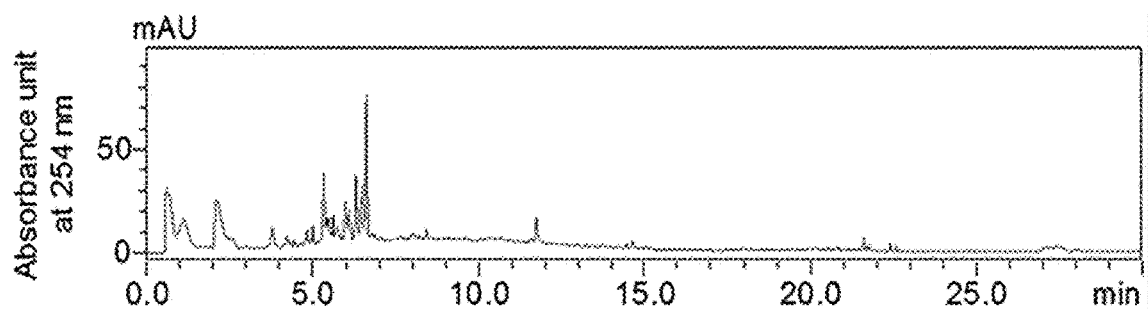
FIG. 5 is a graph showing the HPLC profile of 95% ethanol extract of *Viburnum dilatatum*.

Meanwhile, as a result of comparing graphs of HPLC profiles of 70% ethanol extract (FIGS. 1) and 95% ethanol extract of *Viburnum stellato-tomentosum* (FIG. 2), 95% ethanol extract of *Viburnum lantana* (FIG. 3), 95% ethanol extract of *Viburnum opulus* (FIGS. 4), and 95% ethanol extract of *Viburnum dilatatum* (FIG. 5), which are native to China and Korea and are other plants of the same genus as *Viburnum stellato-tomentosum*, it was confirmed that the components contained in the extracts of *Viburnum stellato-tomentosum* were significantly different from those in the other extracts.

EXAMPLE 2

Preparation of Fraction of *Viburnum stellato-tomentosum*

The 70% ethanol extract of the aerial part of *Viburnum stellato-tomentosum*, prepared in Example 1, was concentrated under reduced pressure and suspended in sterile distilled water, and then the same amount of n-hexane was added thereto, followed by shaking and then leaving to stand. When the solution was separated into an upper layer composed of hexane and a lower aqueous layer, the upper hexane layer was collected. The partition with n-hexane was repeated three times in the same manner. Subsequently, in the same manner, the chloroform and ethyl acetate partitions were sequentially conducted using the aqueous layer, thus preparing the chloroform and ethyl acetate fractions. These fractions were concentrated under reduced pressure to obtain the chloroform and ethyl acetate fractions.

EXAMPLE 3

Evaluation of DPPH Scavenging Activity of *Viburnum stellato-tomentosum* Extract To confirm the antioxidant activities of the extracts and fraction of *Viburnum stellato-tomentosum* prepared in Examples 1 and 2, the DPPH scavenging activities of the extracts and fraction of *Viburnum stellato-tomentosum* were evaluated.

Specifically, a DPPH solution was prepared by dissolving 2,2-diphenyl-2-picrylhydrazyl (DPPH, Sigma, USA) in methanol at a concentration of 0.15 mM. 10 μl of each sample, diluted in methanol, and the DPPH solution were added to a 96-well plate and then allowed to react at room temperature for 40 minutes. The reaction solution was measured for absorbance at 517 nm using a microplate reader 680 (Bio Rad Co., USA), and the DPPH radical scavenging activity of each sample was calculated.

As a result, it was confirmed that the 70% ethanol and 95% ethanol extracts of the aerial, flower, stem, leaf, and fruit parts of *Viburnum stellato-tomentosum* exhibited excellent DPPH free radical scavenging activity at a concentration of 100 μg/ml, and the ethyl acetate fraction of the 70% ethanol extract of the *Viburnum stellato-tomentosum* aerial part exhibited excellent DPPH free radical scavenging activity even at a low concentration of 25 μg/ml (Table 1).

TABLE 1

| | Sample concentration (μg/ml) | DPPH radical scavenging activity (%) |
| --- | --- | --- |
| 70% ethanol extract of *Viburnum stellato-tomentosum* aerial part | 100 | 86.9 ± 2.9 |
| 70% ethanol extract of *Viburnum stellato-tomentosum* flower | 100 | 56.1 ± 1.2 |
| 70% ethanol extract of *Viburnum stellato-tomentosum* stem | 100 | 72.2 ± 0.0 |
| 70% ethanol extract of *Viburnum stellato-tomentosum* leaf | 100 | 68.7 ± 0.2 |
| 70% ethanol extract of *Viburnum stellato-tomentosum* fruit | 100 | 98.1 ± 0.1 |
| 95% ethanol extract of *Viburnum stellato-tomentosum* aerial part | 100 | 59.3 ± 4.3 |
| 95% ethanol extract of *Viburnum stellato-tomentosum* stem | 100 | 75.8 ± 0.7 |
| 95% ethanol extract of *Viburnum stellato-tomentosum* leaf | 100 | 90.4 ± 0.2 |
| 95% ethanol extract of *Viburnum stellato-tomentosum* fruit | 100 | 97.6 ± 0.6 |
| Ethyl acetate fraction of *Viburnum stellato-tomentosum* aerial part | 25 | 68.9 ± 0.7 |

From these results, it was confirmed that the extract and fraction of *Viburnum stellato-tomentosum* exhibited excellent antioxidant activity, suggesting that they may be used for the purpose of preventing skin aging.

EXAMPLE 4

Evaluation of Inhibitory Effect of *Viburnum stellato-tomentosum* Extract on MMP Overexpression 4-1. Cell Culture The CCD-986sk fibroblasts (Korea Cell Line Bank, Korea) were cultured in IMDM (Iscove's Modified Dulbecco's Medium) (Welgene, Korea) containing 10% fetal bovine serum (Atlas, USA), 100 units/ml of penicillin and 100 μg/ml of streptomycin at 37° C. in a humidified 5% $CO_2$ incubator.

4-2. Cytotoxicity Evaluation

To examine whether the *Viburnum stellato-tomentosum* extract is cytotoxic, the viabilities of *Viburnum stellato-tomentosum* extracts were evaluated in cells of Example 4-1.

Specifically, the cells of Example 4-1 were added to each well of a 96-well plate at a concentration of $5 \times 10^3$ cells/100 μl, and cultured in a humidified 5% $CO_2$ incubator at 37° C. After 24 hours, the cells were treated with each of the 70% ethanol extract, 95% ethanol extract and ethyl acetate fraction of *Viburnum stellato-tomentosum* of Examples 1 and 2 at a final concentration of 50 μg/ml or 100 μg/ml together with 100 μl of IMDM. After incubating for 24 hours, 100 μl of the medium was removed from each well, and then 10 μl of Cyto X™ (LPS solution, Korea) was added to each well and allowed to react for 60 minutes. Next, the absorbance was measured using a microplate reader at 450 nm.

Figure 6:
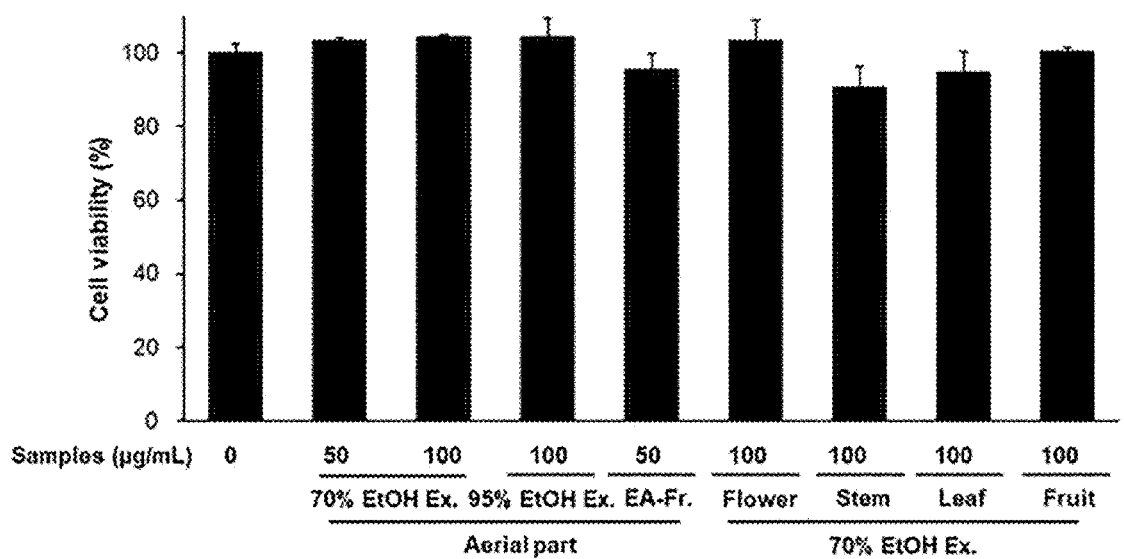
FIG. 6 is a graph showing the results of evaluating cytotoxicity of 70% ethanol extract, 95% ethanol extract or ethyl acetate fraction of the aerial part of *Viburnum stellato-tomentosum,* and 70% ethanol extract of flower, stem, leaf, and fruit parts of *Viburnum stellato-tomentosum* in CCD-986sk skin cells.

As a result, it was confirmed that both the 70% ethanol extract and 95% ethanol extract of the *Viburnum stellato-tomentosum* aerial part showed no cytotoxicity at a concentration of 100 μg/ml, the ethyl acetate fraction of the *Viburnum stellato-tomentosum* aerial part showed no cytotoxicity at a concentration of up to 50 μg/ml, and the 70% ethanol extracts of the flower, stem, leaf, and fruit parts of *Viburnum stellato-tomentosum* also showed no cytotoxicity at a concentration of up to 100 μg/ml (FIG. 6).

4-3. Confirmation of Reduced Production of MMP-1 in CCD-986sk Cells

Matrix metalloproteinase (MMP)-1 is an enzyme that causes skin aging and wrinkle formation by degrading type I, II, and III collagen.

In order to examine whether MMP-1 production in UV-treated CCD-986sk cells is inhibited by treatment with the extract of *Viburnum stellato-tomentosum*, the cells of Example 4-1 irradiated with UV light were treated with the extract of *Viburnum stellato-tomentosum*, and the change in the concentration of MMP-1 was measured.

Specifically, the cells of Example 4-1 were seeded to a 6-well plate at a density of $1.5 \times 10^5$ cells per well and cultured in a humidified 5% $CO_2$ incubator at 37° C. After 24 hours, the cells treated with UVB (UVB) at a dose of 40 mJ/cm$^2$ were cultured for 24 hours with an IMDM supplemented with each of the 70% ethanol extract, 95% ethanol extract and ethyl acetate fraction of the *Viburnum stellato-tomentosum* aerial part or the 70% ethanol extract of each of the flower and leaf parts of *Viburnum stellato-tomentosum*, prepared in Examples 1 and 2, at a final concentration of 50 μg/ml or 100 μg/ml. After culture, the concentration of produced MMP-1 in the supernatant of each well was measured using an MMP-1 ELISA kit (Abcam).

As a result, it was confirmed that the groups treated respectively with the 70% and 95% ethanol extracts of the aerial part of *Viburnum stellato-tomentosum* at a concentration of 100 μg/ml decreased MMP-1 production by 82.0% and 28.6%, respectively, compared to the control group, and that the groups treated respectively with the ethyl acetate fraction of the aerial part of *Viburnum stellato-tomentosum* and the 70% ethanol extracts of the flower and leaf parts of *Viburnum stellato-tomentosum* at a concentration of 50 μg/ml decreased MMP-1 production by 65.9%, 40.4% and 39.8%, respectively, compared to the control group (Table 2).

TABLE 2

| | Sample concentration (μg/ml) | Inhibition (%) of MMP-1 production |
|---|---|---|
| 70% ethanol extract of *Viburnum stellato-tomentosum* aerial part | 50 | 33.4 ± 3.1 |
| | 100 | 82.0 ± 5.4 |
| 95% ethanol extract of *Viburnum stellato-tomentosum* aerial part | 100 | 28.6 ± 3.7 |
| Ethyl acetate fraction of *Viburnum stellato-tomentosum* aerial part | 50 | 65.9 ± 4.4 |
| 70% ethanol extract of *Viburnum stellato-tomentosum* flower | 50 | 40.4 ± 4.9 |
| 70% ethanol extract of *Viburnum stellato-tomentosum* leaf | 50 | 39.8 ± 3.1 |

From these results, it was confirmed that the extracts and fraction of *Viburnum stellato-tomentosum* had an excellent activity on inhibition of MMP-1 production.

4-4. Evaluation of Activity of Regulating Expression of MMP-1. MMP-2 and Collagen Genes in CCD-986sk Cells Evaluation was made as to whether expression of MMP-1, MMP-2, COL1A1 and COL1A2 genes in CCD-986sk cells treated with UV light was regulated by treatment with the extract or fraction of *Viburnum stellato-tomentosum*.

Specifically, the cells of Example 4-1 irradiated with UV light according to the method of Example 4-3 were treated with the *Viburnum stellato-tomentosum* sample for 24 hours. From the treated cell groups, total RNA was isolated using TRI reagent (Ambion) and then synthesized into cDNA using the high-capacity cDNA reverse transcription kit (Applied Biosystems). The cDNA was subjected to real-time PCR amplification in the 7500-Real-Time PCR system (Applied Biosystems, Foster City, CA) using the SYBR Green Master (Roche) based on the property of SYBR Green to be inserted into dsDNA (double strand deoxyribonucleic acid), together with an oligo synthesized to amplify each gene. Results were normalized to actin expression. It was confirmed that the primers used formed about 100 to 200-bp single amplicons in the PCR amplification process. The nucleotide sequences of the primers used are shown in Table 3 below.

Figure 9:
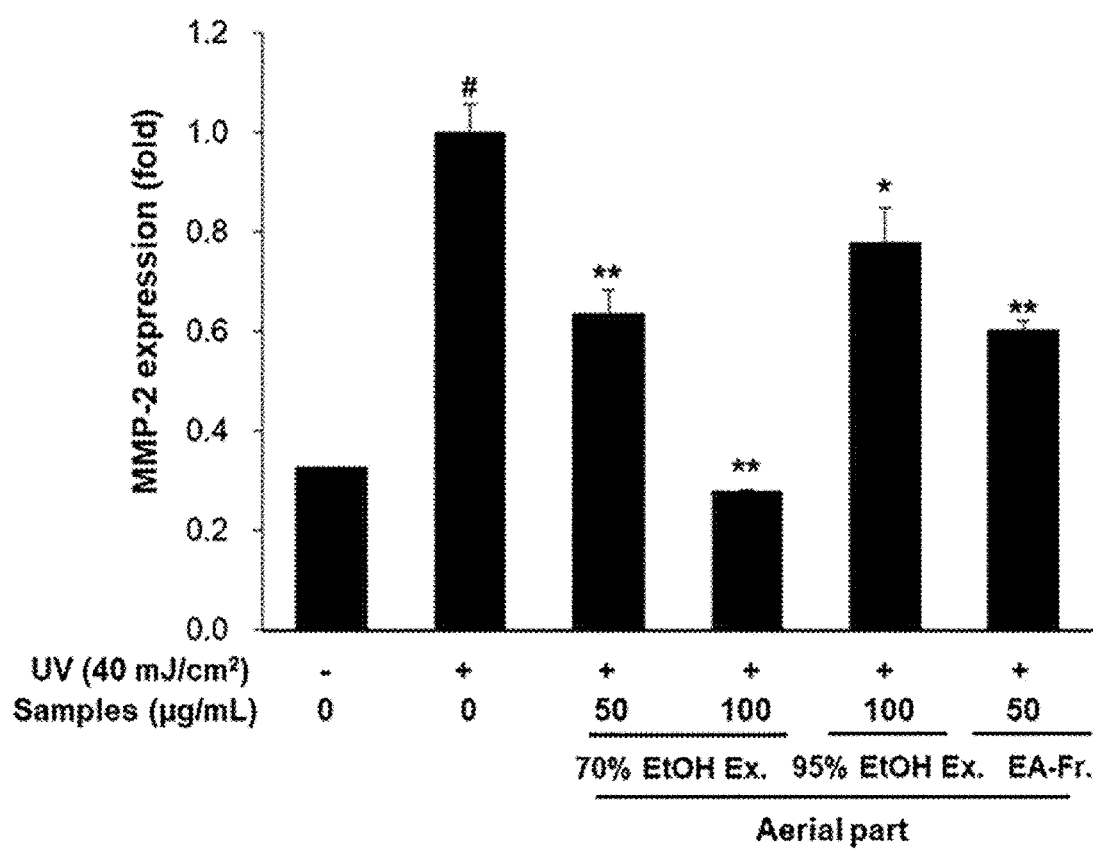
FIG. 9 is a graph showing results indicating that 70% ethanol extract, 95% ethanol extract, and ethyl acetate fraction of the aerial part of *Viburnum stellato-tomentosum* inhibited overexpression of MMP-2 in UV-irradiated CCD-986sk cells.
Figure 10:
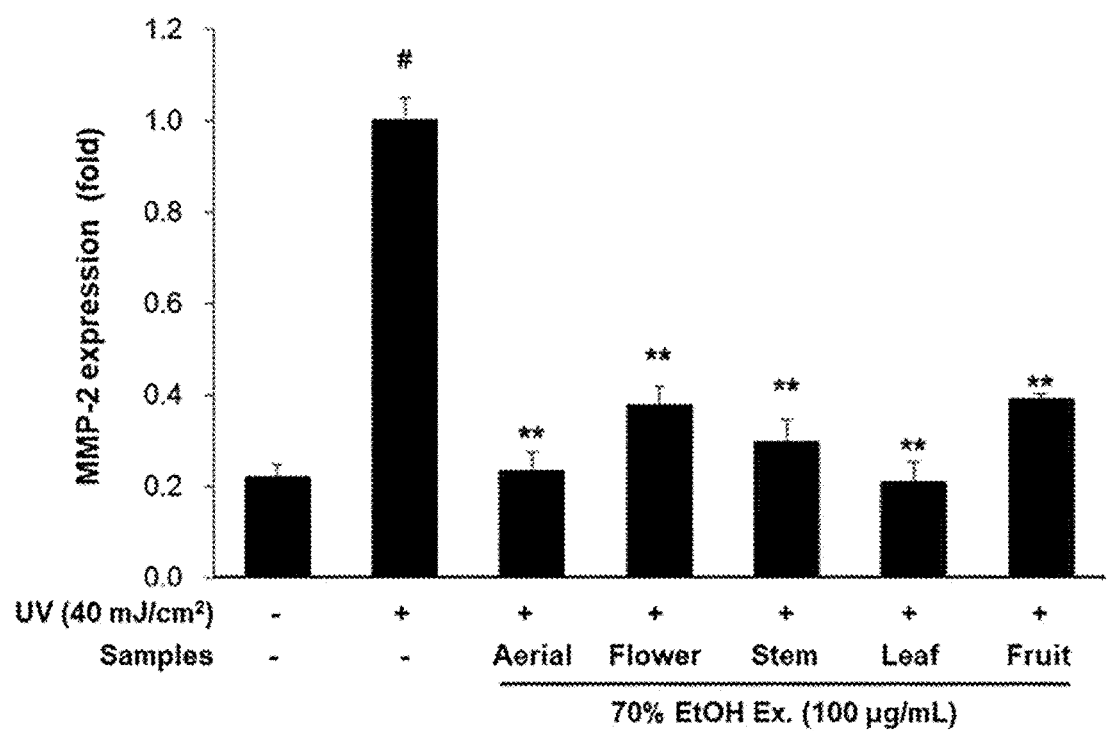
FIG. 10 is a graph showing results indicating that 70% ethanol extract of flower, stem, leaf, and fruit parts of *Viburnum stellato-tomentosum* inhibited overexpression of MMP-2 in UV-irradiated CCD-986sk cells.

70% ethanol extract, 95% ethanol extract, and ethyl acetate fraction of the aerial part of *Viburnum stellato-tomentosum* at a concentration of 50 or 100 μg/ml (FIG. 9). Furthermore, UV-induced MMP-2 overexpression was significantly inhibited by treatment with each of the 70% ethanol extracts of the flower, stem, leaf, and fruit parts of *Viburnum stellato-tomentosum* (FIG. 10).

Figure 11:
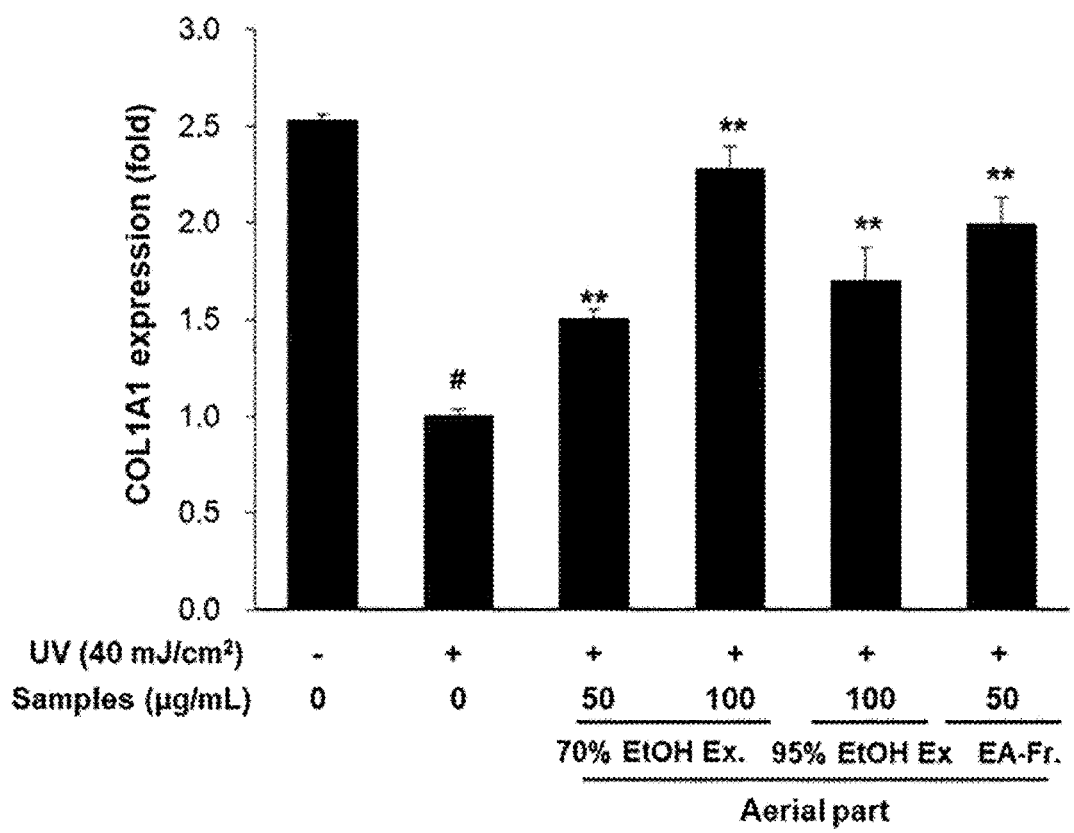
FIG. 11 is a graph showing results indicating that 70% ethanol extract, 95% ethanol extract, and ethyl acetate fraction of the aerial part of *Viburnum stellato-tomentosum* increased COL1A1 expression in UV-irradiated CCD-986sk cells.
Figure 12:
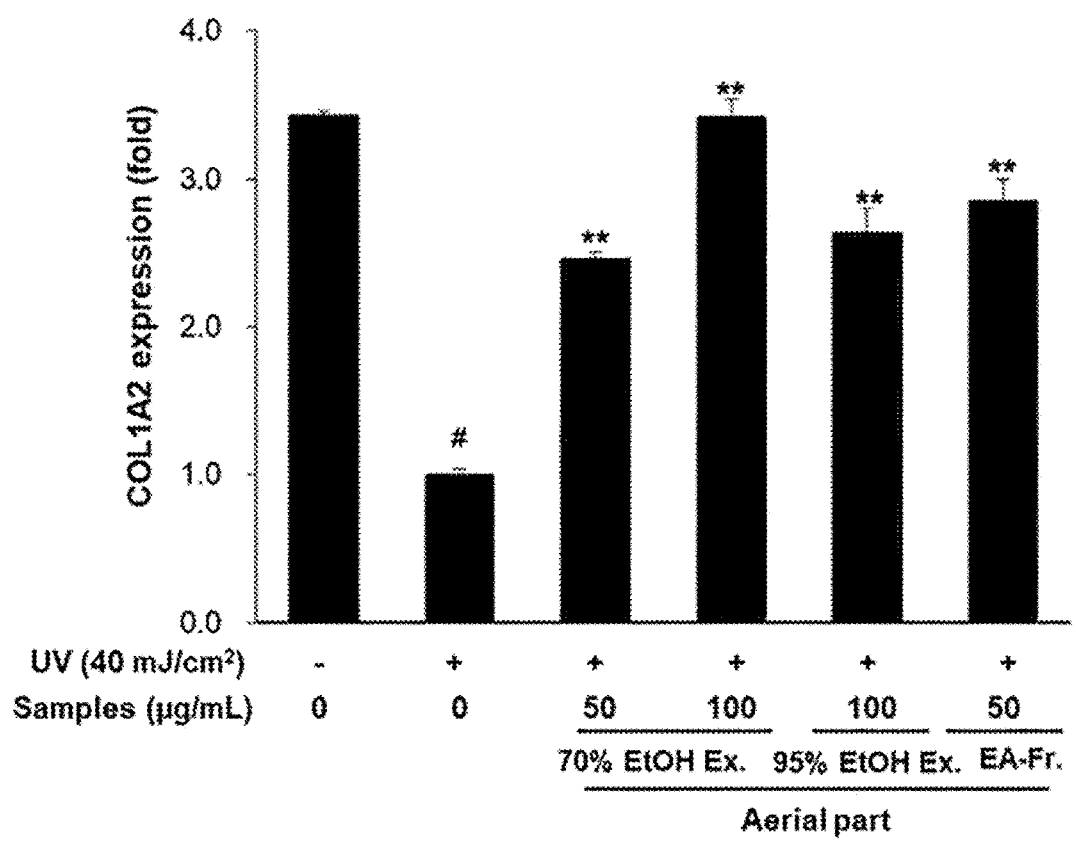
FIG. 12 is a graph showing results indicating that 70% ethanol extract, 95% ethanol extract, and ethyl acetate fraction of the aerial part of *Viburnum stellato-tomentosum* increased COL1A2 expression in UV-irradiated CCD-986sk cells.

Collagen is the targets of MMP-1 and MMP-2. In addition, as a result of analyzing the expression of the collagen genes COL1A1 and COL1A2 genes, it was confirmed that the expression levels of COL1A1 and COL1A2 genes, which were reduced by UV irradiation, were significantly increased by treatment with each of the 70% ethanol extract, 95% ethanol extract, and ethyl acetate fraction of the aerial part of *Viburnum stellato-tomentosum* at a concentration of 50 or 100 μg/ml (FIGS. 11 and 12).

Figure 13:
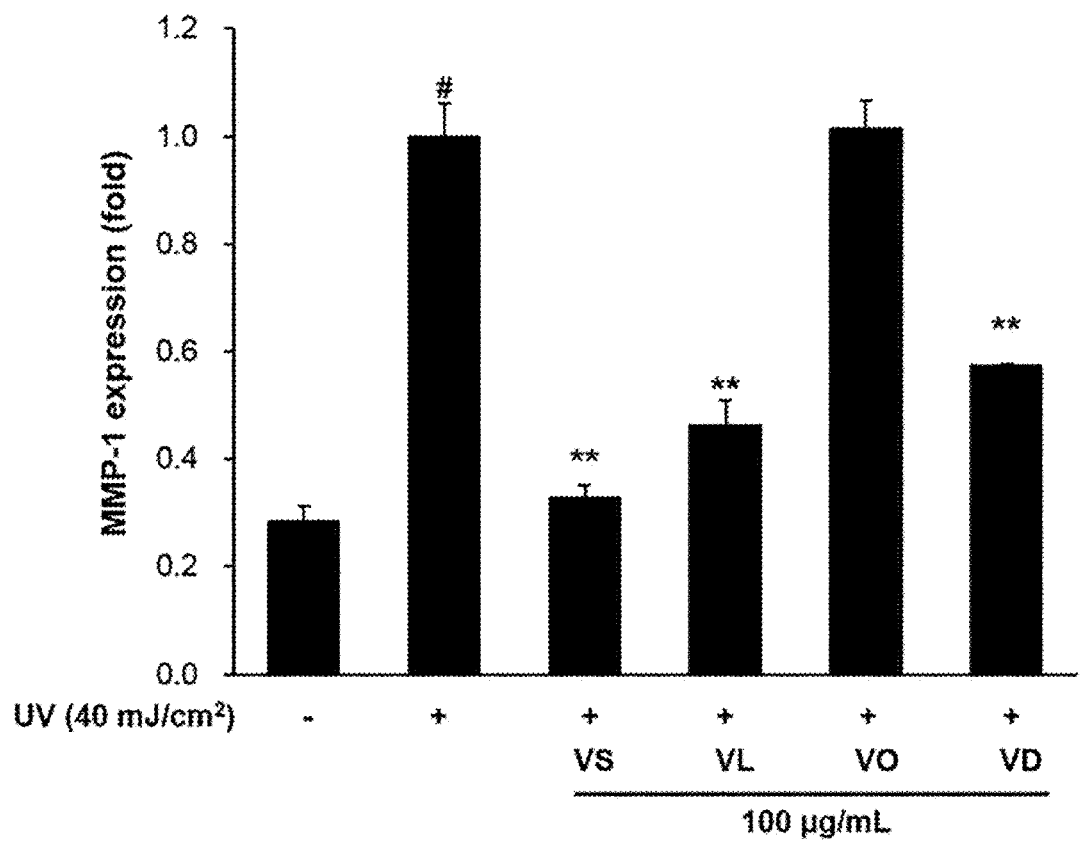
FIG. 13 shows the results of comparing the inhibitory effects of extracts of *Viburnum stellato-tomentosum* and other
*Viburnum* species on MMP-1 expression in UV-irradiated CCD-986sk cells.

In addition, as a result of comparing the MMP-1 expression inhibitory effects of the extracts of *Viburnum stellato-tomentosum* and other plants of the same genus as *Viburnum stellato-tomentosum*, it was confirmed that UV-induced MMP-1 overexpression was more significantly inhibited by treatment with the extract of *Viburnum stellato-tomentosum* than the extract of each of *V. lantana* L., *V. opulus* var. Sargentii (Koehne) Takeda, and *V. dilatatum* Thunb., which are other plants of the same genus as *Viburnum stellato-tomentosum* (FIG. 13).

TABLE 3

| Primer | | Primer nucleotide sequence (5'→3') | SEQ ID NO |
|---|---|---|---|
| Actin | Forward | GGCACCACACCTTCTACAAT | SEQ ID NO: 1 |
| | Reverse | GCCTGGATAGCAACGTACAT | SEQ ID NO: 2 |
| MMP-1 | Forward | AACACATCTGACCTACAGGATTGAAA | SEQ ID NO: 3 |
| | Reverse | CTTGGTGAATGTCAGAGGTGTGA | SEQ ID NO: 4 |
| MMP-2 | Forward | ACTGGAGCAAAAACAAGAAGACATAC | SEQ ID NO: 5 |
| | Reverse | TCCATTTTCTTCTTCACCTCATTG | SEQ ID NO: 6 |
| COL1A1 | Forward | TGGCCTCGGAGGAAACTTT | SEQ ID NO: 7 |
| | Reverse | GCTTCCCCATCATCTCCATTC | SEQ ID NO: 8 |
| COL1A2 | Forward | CGGTGGTGGTTATGACTTTGGT | SEQ ID NO: 9 |
| | Reverse | GAAGGGTCTCAATCTGGTTGTTG | SEQ ID NO: 10 |

Figure 7:
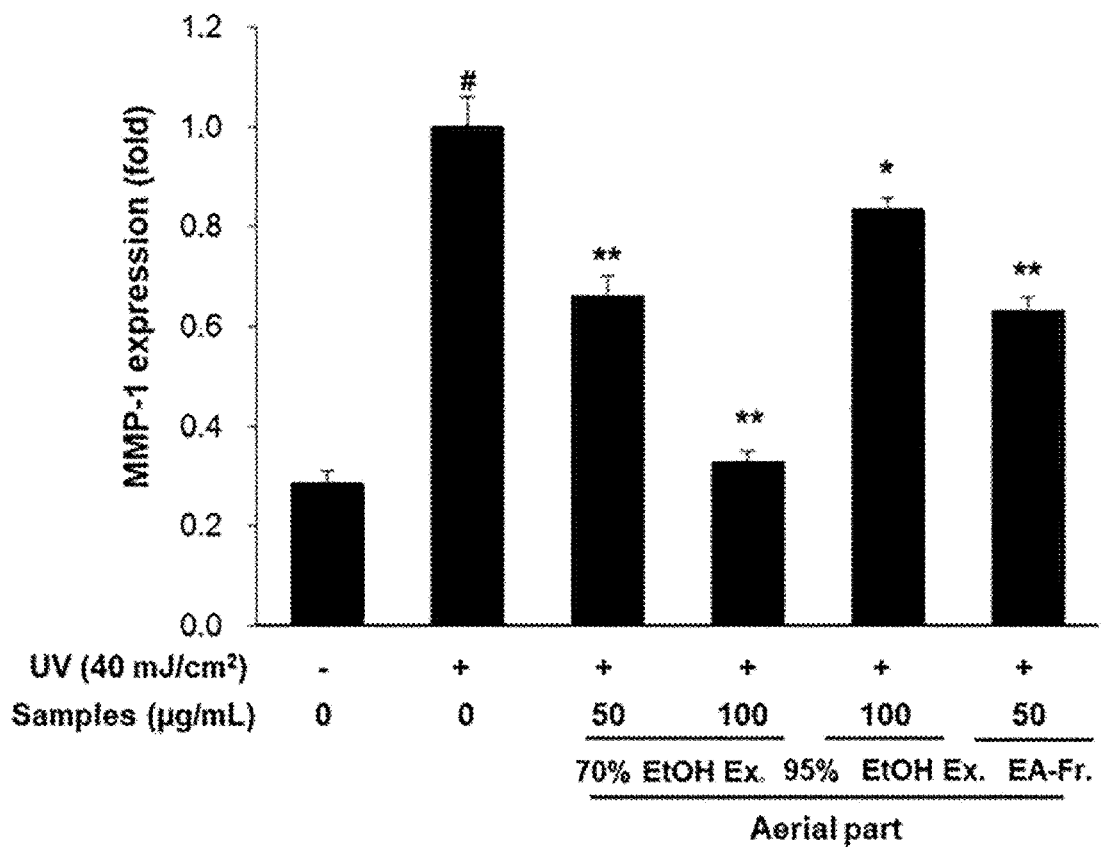
FIG. 7 is a graph showing results indicating that 70% ethanol extract, 95% ethanol extract, and ethyl acetate fraction of the aerial part of *Viburnum stellato-tomentosum* inhibited overexpression of MMP-1 in UV-irradiated CCD-986sk cells.
Figure 8:
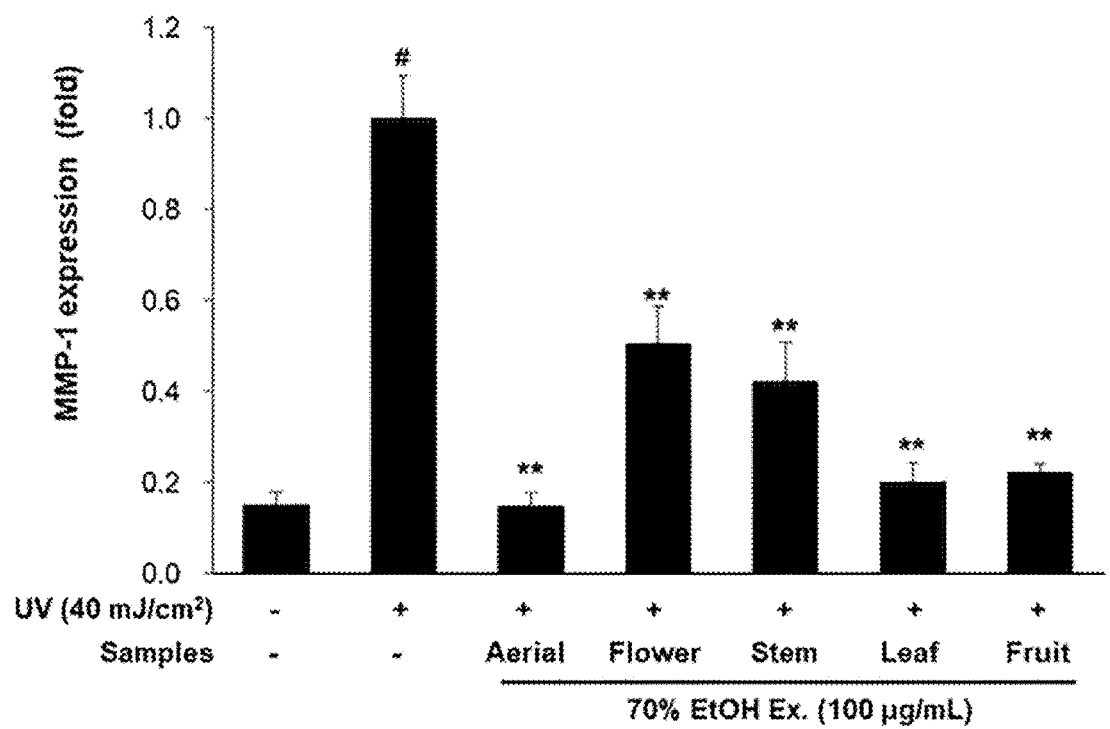
FIG. 8 is a graph showing results indicating that 70% ethanol extract of each of the flower, stem, leaf, and fruit parts of *Viburnum stellato-tomentosum* inhibited overexpression of MMP-1 in UV-irradiated CCD-986sk cells.

As a result, it was confirmed that UV-induced MMP-1 overexpression was significantly inhibited by treatment with each of the 70% ethanol extract, 95% ethanol extract, and ethyl acetate fraction of the aerial part of *Viburnum stellato-tomentosum* at a concentration of 50 or 100 μg/ml (FIG. 7). Furthermore, UV-induced MMP-1 overexpression significantly inhibited by treatment with the 70% ethanol extracts of the flower, stem, leaf, and fruit parts of *Viburnum stellato-tomentosum* (FIG. 8).

It was confirmed that UV-induced MMP-2 overexpression was also significantly reduced by treatment with each of the From these results, it was confirmed that administration of the extract and fraction of *Viburnum stellato-tomentosum* exhibited skin aging preventive and wrinkle formation-reducing effects by inhibiting expression of MMP-1 and MMP-2, which degrade type I, II and III collagen, and increasing expression of COL1A1 and COL1A2 collagen genes.

So far, the present invention has been described with reference to the embodiments. Those of ordinary skill in the art to which the present invention pertains will appreciate that the present disclosure may be embodied in modified

The invention claimed is:

1. A method for preventing skin aging and reducing skin wrinkles, comprising applying a cosmetic composition containing an extract of *Viburnum stellato-tomentosum* to the skin.

2. The method of claim 1, wherein the extract is obtained by extraction with any one solvent selected from the group consisting of water, an alcohol having 1 to 4 carbon atoms, and a mixed solvent thereof.

3. The method of claim 1, wherein the extract is an ethanol extract or a methanol extract.

4. The method of claim 1, wherein the extract is an ethyl acetate fraction of an ethanol extract of *Viburnum stellato-tomentosum*.

5. The method of claim 1, wherein the skin aging and the skin wrinkles are caused by skin exposure to UV rays.

6. The method of claim 1, wherein the skin aging and the skin wrinkles are caused by overexpression of MMP-1 or MMP-2.

7. The method of claim 1, wherein the skin aging and the skin wrinkles are caused by inhibition of COL1A1 or COL1A2 expression.

8. The method of claim 1, wherein the cosmetic composition is any one formulation selected from the group consisting of a solution, suspension, emulsion, paste, gel, cream, lotion, powder, soap, surfactant-containing cleansing, oil, powder foundation, emulsion foundation, wax foundation, and spray.

* * * * *